US012678032B2

(12) United States Patent (10) Patent No.: US 12,678,032 B2
Inoue et al. (45) Date of Patent: Jul. 14, 2026

(54) ENDOSCOPE

(71) Applicant: FUJIFILM Corporation, Tokyo (JP)

(72) Inventors: Masaya Inoue, Kanagawa (JP);
Takashi Harada, Kanagawa (JP)

(73) Assignee: FUJIFILM Corporation, Tokyo (JP)

( * ) Notice: Subject to any disclaimer, the term of this
patent is extended or adjusted under 35
U.S.C. 154(b) by 310 days.

(21) Appl. No.: 18/450,357

(22) Filed: Aug. 15, 2023

(65) Prior Publication Data

US 2023/0389780 A1 Dec. 7, 2023

Related U.S. Application Data

(63) Continuation of application No.
PCT/JP2022/005886, filed on Feb. 15, 2022.

(30) Foreign Application Priority Data

Feb. 18, 2021 (JP) ................................. 2021-024398

(51) Int. Cl.
*A61B 1/005* (2006.01)
*A61B 1/008* (2006.01)
*A61B 1/01* (2006.01)
(52) U.S. Cl.
CPC ............ *A61B 1/0055* (2013.01); *A61B 1/008*
(2013.01); *A61B 1/01* (2013.01)
(58) Field of Classification Search
CPC ......... A61B 1/0055; A61B 1/008; A61B 1/01;
G02B 23/24; G02B 23/25; G02B 23/26
See application file for complete search history.

(56) References Cited

U.S. PATENT DOCUMENTS

2001/0037051 A1* 11/2001 Fujii ................... A61B 1/0052
600/146
2007/0167679 A1 7/2007 Miyamoto et al.
2007/0232857 A1 10/2007 Otawara
(Continued)

FOREIGN PATENT DOCUMENTS

JP 2004129785 4/2004
JP 2006015018 1/2006
(Continued)

OTHER PUBLICATIONS

"International Search Report (Form PCT/ISA/210) of PCT/JP2022/
005886", mailed on May 10, 2022, with English translation thereof,
pp. 1-5.
(Continued)

*Primary Examiner* — Michael J Carey
*Assistant Examiner* — Megan Elizabeth Monahan
(74) *Attorney, Agent, or Firm* — JCIPRNET

(57) ABSTRACT

An elevating base provided to be movable between an
elevated position and a fallen position is provided at a distal
end of an insertion part of the endoscope. As an elevating
operation lever rotates in a first direction, the elevating
operation lever causes the elevating base to move to the
elevated position, and as the elevating operation lever
rotates in a second direction, the elevating operation lever
causes the elevating base to move to the fallen position. The
elevating operation lever is coupled to a bearing member via
a rotation ring. The rotation ring has a protrusion, and the
bearing member has a plurality of holes and a rail to
configure a locking mechanism.

6 Claims, 13 Drawing Sheets

(56)  References Cited

U.S. PATENT DOCUMENTS

| | | | |
|---|---|---|---|
| 2008/0287737 | A1 | 11/2008 | Dejima |
| 2009/0036736 | A1 | 2/2009 | Dejima et al. |
| 2011/0077461 | A1* | 3/2011 | Maruyama ......... A61B 1/00133 |
| | | | 600/107 |
| 2015/0148598 | A1 | 5/2015 | Fukushima et al. |
| 2015/0313449 | A1 | 11/2015 | Stand et al. |
| 2016/0089004 | A1* | 3/2016 | Morimoto .......... A61B 1/00066 |
| | | | 600/107 |

FOREIGN PATENT DOCUMENTS

| | | |
|---|---|---|
| JP | 2009183699 | 8/2009 |
| JP | 2011072455 | 4/2011 |
| JP | 2015104424 | 6/2015 |
| JP | 2020137947 | 9/2020 |

OTHER PUBLICATIONS

"Written Opinion of the International Searching Authority (Form PCT/ISA/237) of PCT/JP2022/005886", mailed on May 10, 2022, with English translation thereof, pp. 1-6.

* cited by examiner

ENDOSCOPE

CROSS-REFERENCE TO RELATED APPLICATIONS

This application is a Continuation of PCT International Application No. PCT/JP2022/005886 filed on 15 Feb. 2022, which claims priority under 35 U.S.C § 119(a) to Japanese Patent Application No. 2021-024398 filed on 18 Feb. 2021. The above application is hereby expressly incorporated by reference, in its entirety, into the present application.

BACKGROUND OF THE INVENTION

1. Field of the Invention

The present invention relates to an endoscope that changes a lead-out direction of a treatment tool.

2. Description of the Related Art

Endoscopes for use in the medical field are used not only for observation of the inside of a subject but also for various treatments on an observation site. The endoscope includes an insertion part to be inserted into a subject and an operation part provided to be continuous with a proximal end portion of the insertion part. Various treatment tools, such as a forceps and an incision tool, are inserted into a treatment tool channel in the insertion part from a treatment tool lead-in port provided in the operation part of the endoscope and are led out of a treatment tool lead-out port opened at a distal end part of the insertion part, whereby various treatments, such as resection and collection of an observation site, are performed.

It is necessary to change a lead-out direction of the treatment tool to be led out from the treatment tool lead-out port of the endoscope in order to treat a desired position in the subject. Therefore, an elevating base that changes a lead-out direction of the treatment tool is provided at the distal end part of the insertion part. By operating an elevating operation lever provided on the operation part, a posture of the elevating base is moved between a fallen position and an elevated position. Moving the elevating base from the fallen position to the elevated position enables the elevating base to guide the treatment tool and change the lead-out direction of the treatment tool (see JP2020-137947A).

Additionally, in the endoscope recited in JP2006-015018A (corresponding to US2007/232857A1), a slit into which a guide wire is fit is formed in an elevating base. The guide wire is inserted into a treatment tool channel together with a treatment tool to guide the treatment tool. Then, in a case where the elevating base reaches an elevated position, the guide wire is fitted into the slit of the elevating base to fix the elevating base. As a result, an elevating operation lever that moves in conjunction with the elevating base is also fixed.

Meanwhile, in the endoscope recited in JP2011-072455A (corresponding to US2011/0077461A1), a friction resistance applying spring material is attached to an elevating operation lever. In a state of being pressed against a fixed wall formed on an operation part, the friction resistance applying spring material rotates integrally with the elevating operation lever. A lubricant is applied between the friction resistance applying spring material and the fixed wall. The friction resistance applying spring material is pressed against the fixed wall by an elastic force to generate frictional resistance. When a user releases his/her hand from the elevating operation lever, the elevating operation lever is temporarily stopped due to frictional resistance.

SUMMARY OF THE INVENTION

When a treatment is performed using an endoscope, a case may occur where a user wants to stop a lead-out direction of a treatment tool in a desired direction and perform the treatment with the lead-out direction maintained. Therefore, it is desired to stop an elevating base not only at an elevated position or a fallen position but also in the middle between the elevated position and the fallen position.

However, in the endoscopes recited in JP2020-137947A and JP2006-015018A, stopping the elevating base in the middle between the elevated position and the fallen position is not taken into consideration. In particular, in the endoscope recited in JP2006-015018A, the guide wire is fixed to stop the elevating base and the elevating operation lever only when the elevating base is at the elevated position, and cannot be fixed when the elevating base is at other positions. Furthermore, in this case, even if the elevating operation lever is pressed by a finger or the like, the elevating operation lever will be moved by a reaction force from the treatment tool.

Furthermore, in the endoscope recited in JP2011-072455A, although when the user releases his/her hand from the elevating operation lever, the elevating operation lever is temporarily stopped by frictional resistance between the friction resistance applying spring material and the fixed wall, and when a treatment is performed using a treatment tool having high rigidity, such as a stent or a puncture needle, the elevating operation lever receives too great a reaction force from the treatment tool to maintain a stopped state only with the frictional resistance. As a result, the elevating base is moved in conjunction with the elevating operation lever, so that the lead-out direction of the treatment tool also deviates.

The present invention has been made in view of the above circumstances, and an object of the present invention is to provide an endoscope capable of maintaining a lead-out direction of a treatment tool at a desired direction and performing various treatments while the lead-out direction is maintained.

An endoscope according to an aspect of the present invention includes an insertion part, an operation part, a distal end part main body, an elevating base, an elevating operation lever, a bearing member, a coupling member, and a locking mechanism, in which in a case where a protrusion is fitted to a hole, the elevating operation lever is locked at a first position, and in a case where the elevating operation lever is rotated in a first direction or a second direction, the protrusion passes through an elastically deformed rail and moves to a hole at a position different from the first position to lock the elevating operation lever at a second position. The insertion part is inserted into a subject. The operation part is provided at a proximal end of the insertion part. The distal end part main body is positioned at a distal end of the insertion part and communicates with a treatment tool lead-out port. The elevating base is an elevating base that is provided on the distal end part main body and that causes a treatment tool led out from the treatment tool lead-out port to elevate, and is provided to be movable between an elevated position and a fallen position. As the elevating operation lever rotates in a first direction, the elevating operation lever causes the elevating base to move to the elevated position, and as the elevating operation lever rotates in a second direction, the elevating operation lever causes the elevating base to move to the fallen position. The bearing member is provided in the operation part. The coupling member couples the elevating operation lever and the bearing member to each other. The locking mechanism is provided between the bearing member and the coupling member, and includes a plurality of protrusions, a plurality of holes, and a rail. The plurality of protrusions are provided on one of the bearing member and the coupling member. The plurality of holes are provided on the other of the bearing member and the coupling member. The rail is positioned between adjacent holes.

The holes and the protrusions are formed at the same pitch, and the number of the protrusions is smaller than the number of the holes. Preferably, one of the bearing member and the coupling member has the protrusions formed along a first arc positioned around a center axis, and the other of the bearing member and the coupling member has the holes formed along a second arc that is positioned around the center axis, that has a radius equal to a radius of the first arc, and that has an arc length longer than an arc length of the first arc.

It is preferable that an inner diameter of the hole is formed to gradually decrease from an intermediate portion of the second arc toward both ends of the second arc. It is preferable that the insertion part includes a bendable part, and an angle knob that curves the bendable part is attached to the bearing member.

It is preferable that at least some components are disposable.

According to the present invention, it is possible to provide an endoscope capable of maintaining a lead-out direction of a treatment tool at a desired direction and performing various treatments while the lead-out direction is maintained.

BRIEF DESCRIPTION OF THE DRAWINGS

FIG. 3 is a perspective view illustrating a distal end part of the endoscope.

FIG. 4 is an exploded perspective view of the distal end part of the endoscope.

DESCRIPTION OF THE PREFERRED EMBODIMENTS

Figure 1:
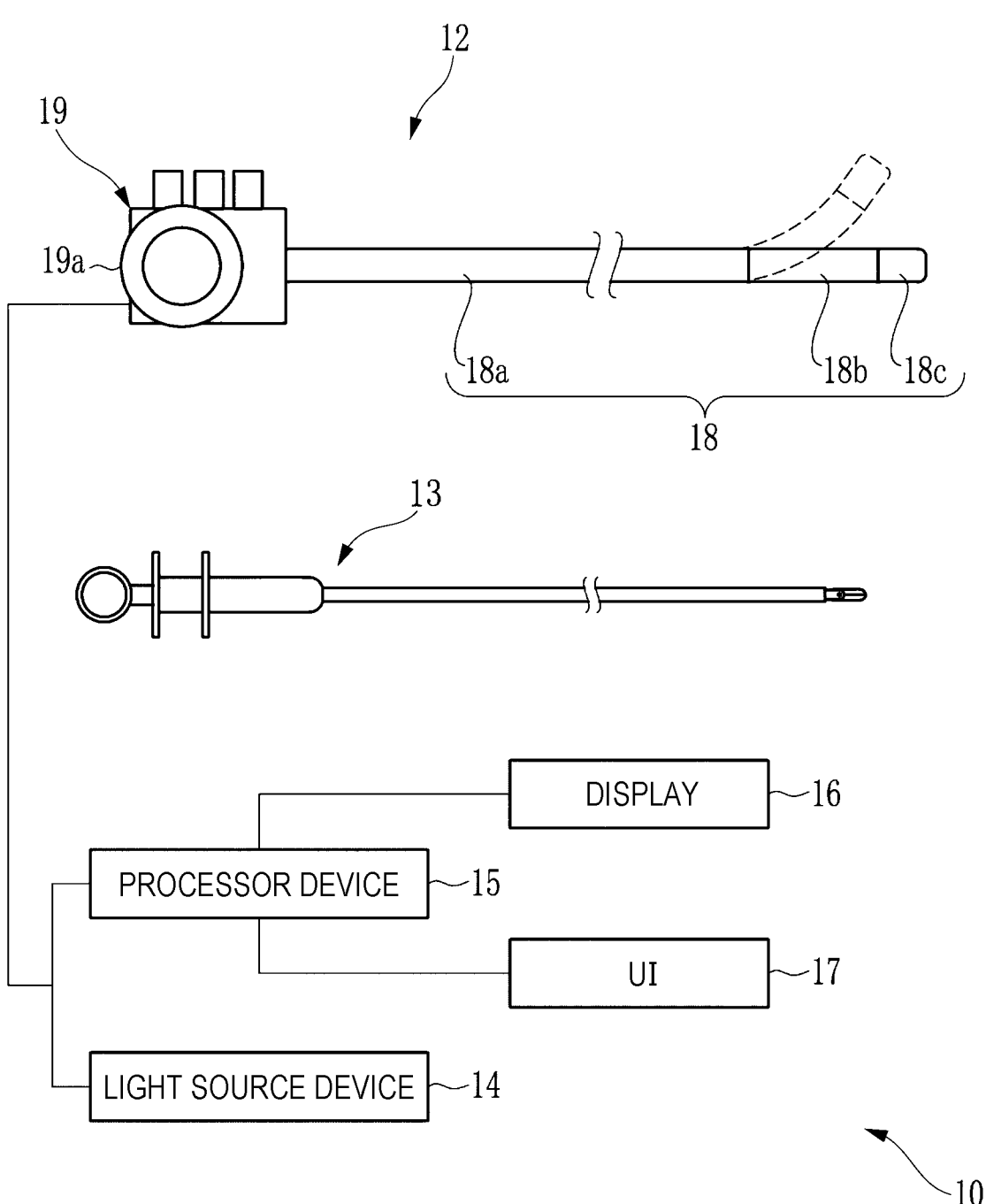
FIG. 1 is a schematic view illustrating a configuration of an endoscope system.

As shown in FIG. 1, an endoscope system 10 includes an endoscope 12, a treatment tool 13, a light source device 14, a processor device 15, a display 16, and a user interface (UI) 17. The endoscope 12 images an observation target. The light source device 14 emits illumination light which illuminates the observation target. The processor device 15 performs system control of the endoscope system 10. The display 16 is a display part that displays an observation image or the like based on an endoscope image. The UI 17 has a keyboard, a mouse, a touch pad, a microphone, and the like, and receives input operation by a doctor as a user.

It is preferable that at least some of the components configuring the endoscope 12 are formed of a resin material, a rubber material, a metal material, or the like, and are discarded as disposable. In addition, in a case of a metal material, it is more preferable to form a component by means of metal injection molding.

The endoscope 12 is optically connected to the light source device 14 and is electrically connected to the processor device 15. The endoscope 12 has an insertion part 18 to be inserted into a subject and an operation part 19 provided at a proximal end of the insertion part 18. The insertion part 18 includes a flexible part 18a, a bendable part 18b, and a distal end part 18c which are provided to be continuous in this order from the proximal end toward a distal end. By operating an angle knob 19a of the operation part 19, the bendable part 18b is curved. As a result, the distal end part 18c faces a desired direction.

Figure 2:
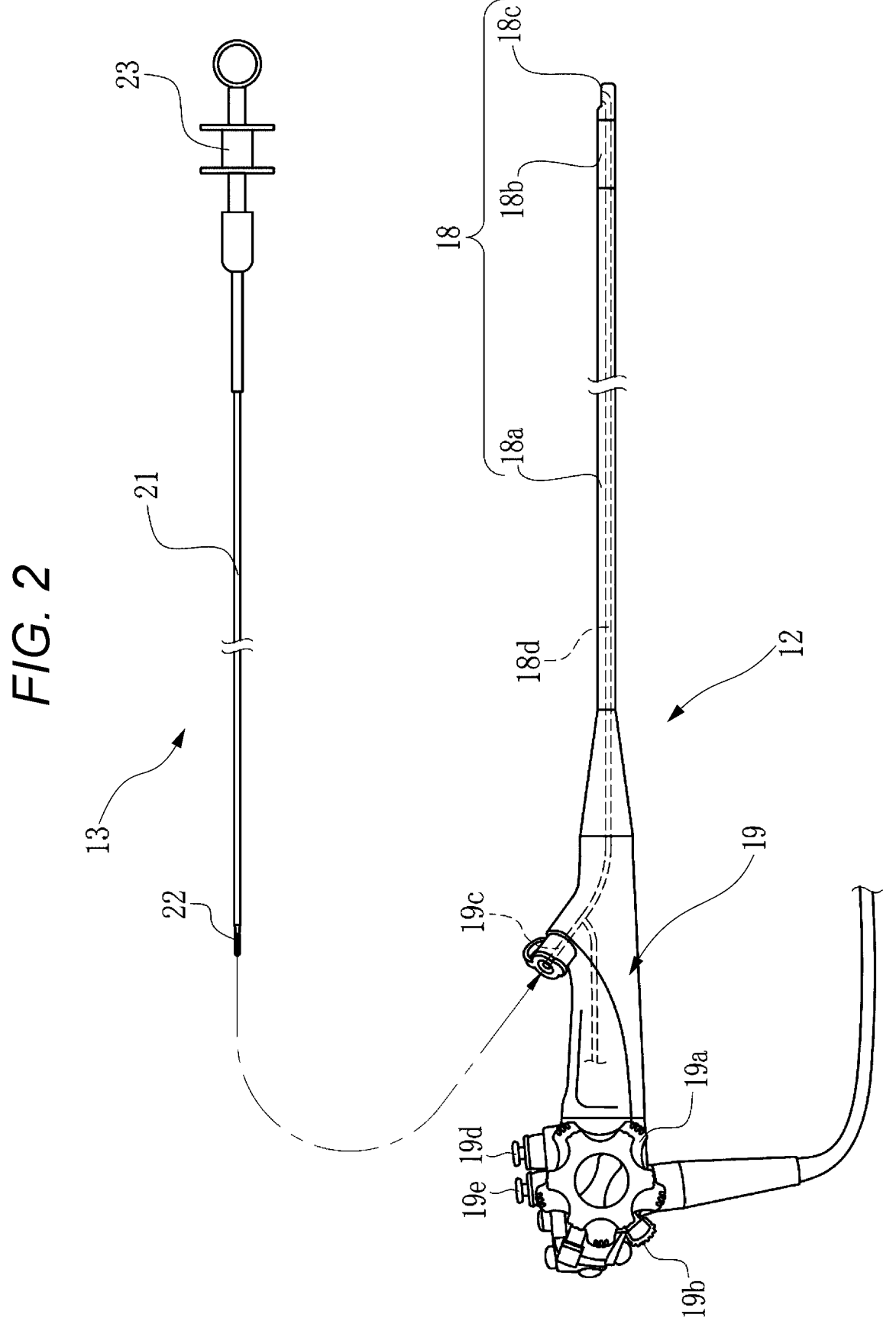
FIG. 2 is an external view of an endoscope and a treatment tool.

As shown in FIG. 2, the operation part 19 is provided with an elevating operation lever 19b, a treatment tool lead-in port 19c, an air/water supply button 19d, and a suction button 19e, in addition to the angle knob 19a. The treatment tool lead-in port 19c is an inlet for inserting the treatment tool 13. The treatment tool 13 inserted into the treatment tool lead-in port 19c is guided to an elevating base accommodation part 41 (refer to FIG. 4) of the distal end part 18c.

By operating the elevating operation lever 19b, a treatment tool elevating mechanism 45 to be described later operates to rotate an elevating base 33. Rotation of the elevating base 33 causes an advancing direction of the treatment tool 13 guided to the elevating base accommodation part 41 to be curved and guided in a direction toward an opening window 32C on an upper surface side of the elevating base accommodation part 41, thereby causing the treatment tool 13 to be led out of the opening window 32C.

Figure 3:
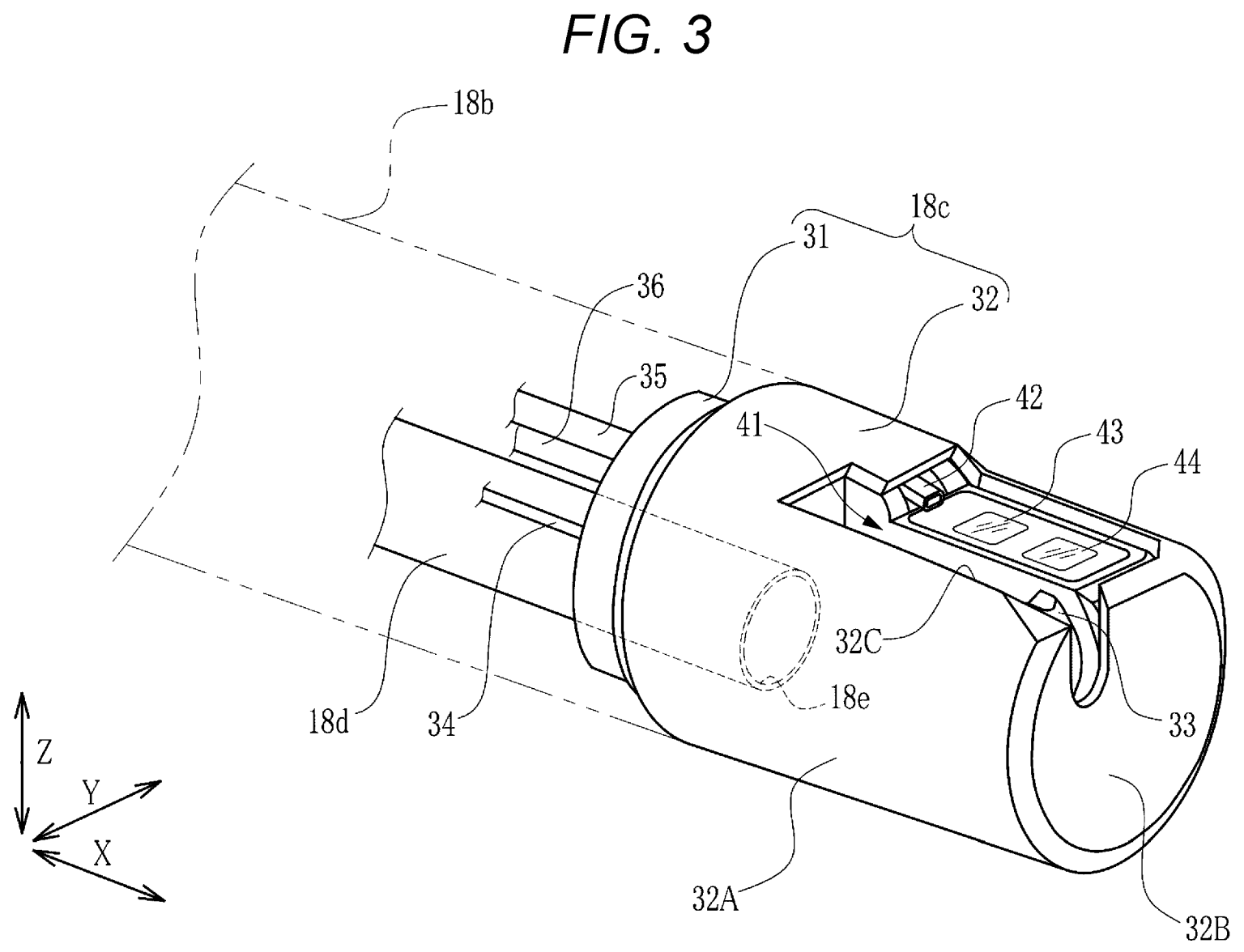
Figure 4:
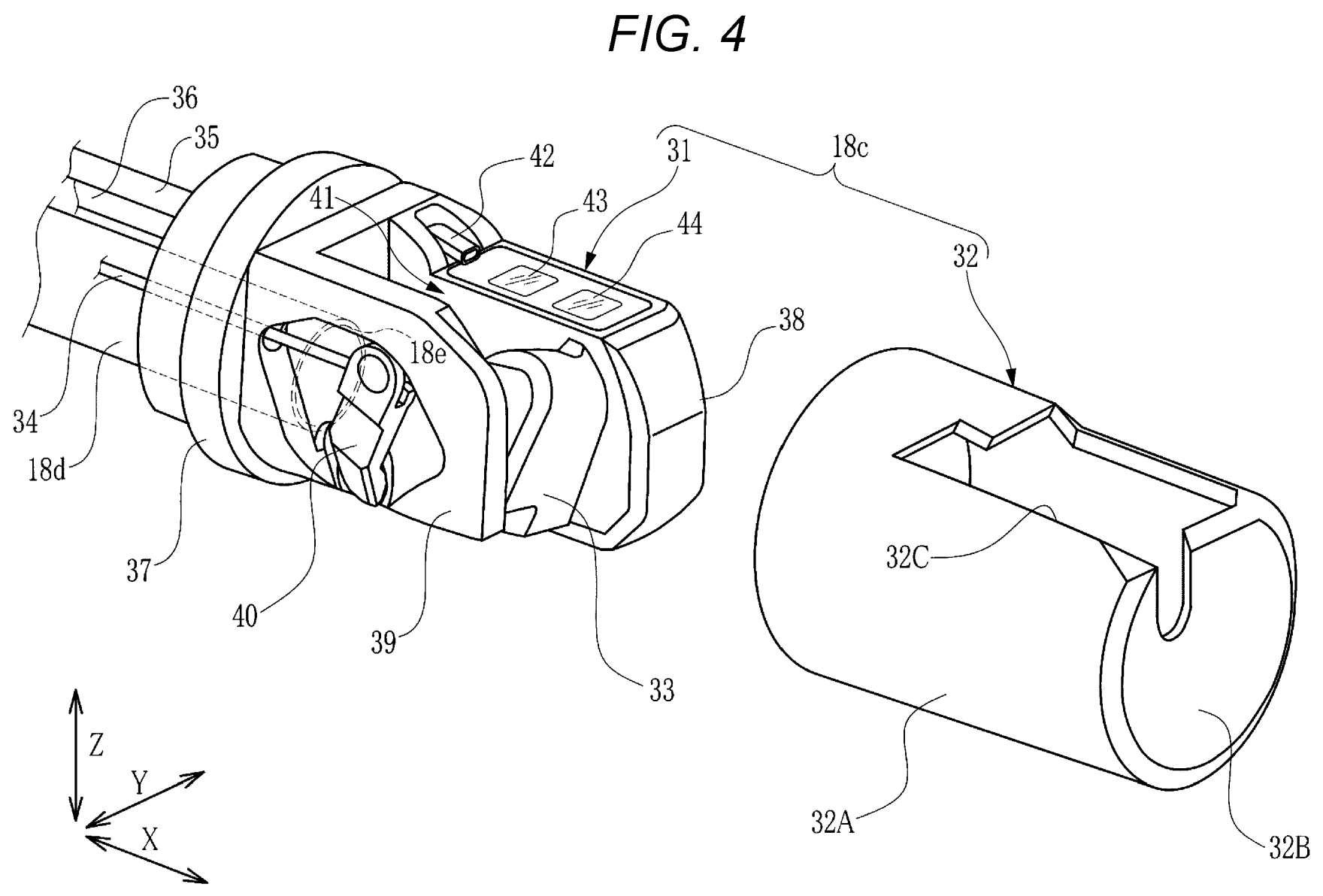

When the air/water supply button 19d is operated, air and water are supplied to an air/water supply tube (not shown) to jet air and water from an air/water supply nozzle 42 provided in a distal end part main body 31 (refer to FIGS. 3 and 4). In addition, when the suction button 19e is operated, body fluids, such as blood, can be suctioned via a treatment tool channel 18d from a suction port that also serves as a treatment tool lead-out port 18e (refer to FIGS. 3 and 4) disposed in the distal end part main body 31.

An image sensor 43, an illumination optical system 44, and the like, which will be described later, are provided in the distal end part 18c. The image sensor 43 is preferably a charge-coupled device (CCD) image sensor, a complementary metal-oxide-semiconductor (CMOS) image sensor, or the like.

The processor device 15 is electrically connected to the display 16 and the UI 17. The processor device 15 performs image processing and the like on an endoscope image captured by the image sensor 43 and causes the display 16 to display the endoscope image.

The treatment tool channel 18d for insertion of the treatment tool 13 is disposed in the insertion part 18. The treatment tool channel 18d has one end connected to the distal end part main body 31, and the other end connected to the treatment tool lead-in port 19*c* provided in the operation part 19.

The treatment tool 13 is a treatment tool for an endoscope that is inserted into a subject together with the insertion part 18 through the treatment tool channel 18*d*. As the treatment tool 13, for example, a biopsy forceps, a snare, a stent, a puncture needle, a high-frequency treatment tool, an ultrasonic treatment tool, or the like is combined with the endoscope 12.

The treatment tool 13 includes a flexible sheath 21, an operation wire (not shown), a distal end part 22, and an operation part 23. The flexible sheath 21 is a tubular sheath formed of a flexible material, for example, a soft resin, and is inserted into the treatment tool channel 18*d* of the endoscope 12. The operation wire is provided integrally with the distal end part 22 and is inserted into the flexible sheath 21.

The distal end part 18*c* has the distal end part main body 31 and a cap 32 as shown in FIGS. 3 and 4, and is configured by attachment of the cap 32 to the distal end part main body 31. The configuration of the distal end part 18*c* is not limited thereto, and the distal end part main body 31 and the cap 32 may be integrally fixed to each other so as not to be detached by a user. The distal end part main body 31 is provided on a distal end side of the insertion part 18 (refer to FIG. 1), and the elevating base 33 is provided at the distal end part main body 31.

The endoscope 12 is a side-viewing endoscope used as, for example, a duodenoscope, and the distal end part 18*c* shown in FIGS. 3 and 4 has a configuration in the side-viewing endoscope. FIGS. 3 and 4 show the treatment tool channel 18*d*, an elevating operation wire 34, a signal cable 35, and a light guide 36 which are disposed inside the insertion part 18 of the endoscope 12. The treatment tool channel 18*d* guides the distal end part of the treatment tool 13 to the distal end part main body 31. The elevating operation wire 34 is an operation wire for performing operation of rotating the elevating base 33. Illustration of an air/water supply channel and the like connected to the air/water supply nozzle 42 is omitted to prevent complication.

The cap 32 has a distal end side sealed and formed to be substantially tubular, and has a peripheral surface portion 32A and an end surface portion 32B. The substantially rectangular opening window 32C is formed in a part of the peripheral surface portion 32A. In the example shown in FIGS. 3 and 4, the opening window 32C is an opening portion notched from the peripheral surface portion 32A to the end surface portion 32B. Hereinafter, a center axis direction of the distal end part main body 31 and the cap 32 will be described as an X-axis direction, an up-down direction orthogonal to the X-axis direction will be described as a Z-axis direction, and a left-right direction orthogonal to both the X-axis direction and the Z-axis direction will be described as a Y-axis direction.

When the cap 32 is attached to the distal end part main body 31, the cap 32 covers the elevating base accommodation part 41 to be described later, and the opening window 32C is opened toward the Z-axis direction. This allows the treatment tool lead-out port 18*e* of the treatment tool channel 18*d* to communicate with the opening window 32C through the elevating base accommodation part 41. The image sensor 43 and the illumination optical system 44 are exposed through the opening window 32C. The cap 32 is coaxially attached to the distal end part main body 31.

The cap 32 is made of an elastic material, for example, a rubber material such as fluororubber or silicone rubber, or a resin material such as polysulfone or polycarbonate. The configuration of the distal end part 18*c* is not limited thereto, and the distal end part main body 31 and the cap 32 may be integrally fixed to each other so as not to be detached by a user. A convex-shaped engagement part (not shown) to be engaged with a groove-shaped engaged part (not shown) formed on the distal end part main body 31 is provided on a proximal end side of the cap 32, and engaging the engagement part with the engaged part results in detachably attaching the cap 32 to the distal end part main body 31.

As illustrated in FIG. 4, the distal end part main body 31 has a disk part 37 and a pair of partition wall parts 38 and 39. The distal end part main body 31 is made of, for example, a resin material. The pair of partition wall parts 38 and 39 is provided to protrude from the disk part 37 in the X-axis direction. These partition wall parts 38 and 39 are arranged so as to be opposed to each other in the Y-axis direction. In addition, the above-described elevating base accommodation part 41 accommodating the elevating base 33 is provided between the partition wall part 38 and the partition wall part 39. The elevating base accommodation part 41 is opened in the Z-axis direction.

The elevating base accommodation part 41 communicates with the treatment tool lead-out port 18*e* of the treatment tool channel 18*d*. The elevating base 33 causes the treatment tool 13 led out of the treatment tool lead-out port 18*e* to elevate. The elevating base 33 is rotatably attached inside the elevating base accommodation part 41 via a rotation shaft member 40 (refer to FIGS. 4 and 5), and is movable between an elevated position (a position indicated by a chain double-dashed line) and a fallen position (a position indicated by a solid line). A distal end of the elevating operation wire 34 is coupled to an end portion of the rotation shaft member 40. As the elevating operation wire 34 is pushed and pulled, the elevating base 33 rotationally moves from the fallen position to the elevated position. This enables change of a lead-out direction of the distal end part 22 of the treatment tool 13 led out to the treatment tool lead-out port 18*e*.

The disk part 37 is coupled to a distal end side of the bendable part 18*b*. The bendable part 18*b* is configured by covering an outer periphery of a structure having a plurality of rotatably coupled curved pieces with a tubular net body, a rubber outer skin, or the like. The disk part 37 is fixed to a curved piece positioned on the most distal end side among the plurality of curved pieces constituting the bendable part 18*b* by, for example, screwing or adhesion using an adhesive.

The partition wall part 38 is disposed adjacent to the elevating base accommodation part 41 in the Y-axis direction. The partition wall part 38 includes the air/water supply nozzle 42, the image sensor 43, and the illumination optical system 44. The image sensor 43 is electrically connected to the signal cable 35, and the illumination optical system 44 is optically connected to the light guide 36. The air/water supply nozzle 42 is provided at the distal end part main body 31 toward the image sensor 43 and the illumination optical system 44, and accordingly, the image sensor 43 and the illumination optical system 44 are cleaned by air and water jetted from the air/water supply nozzle 42.

The signal cable 35 and the light guide 36 are respectively connected to the processor device 15 and the light source device 14 through the insertion part 18, the operation part 19, a connector (not shown), and the like. The processor device 15 performs image processing and the like on an imaging signal acquired by the image sensor 43 and causes the display 16 to display an observation image. The light guide 36 is configured with an optical fiber cable or the like, transmits illumination light emitted from the light source device 14, and irradiates an observation target with the illumination light through the illumination optical system 44.

Figure 5:
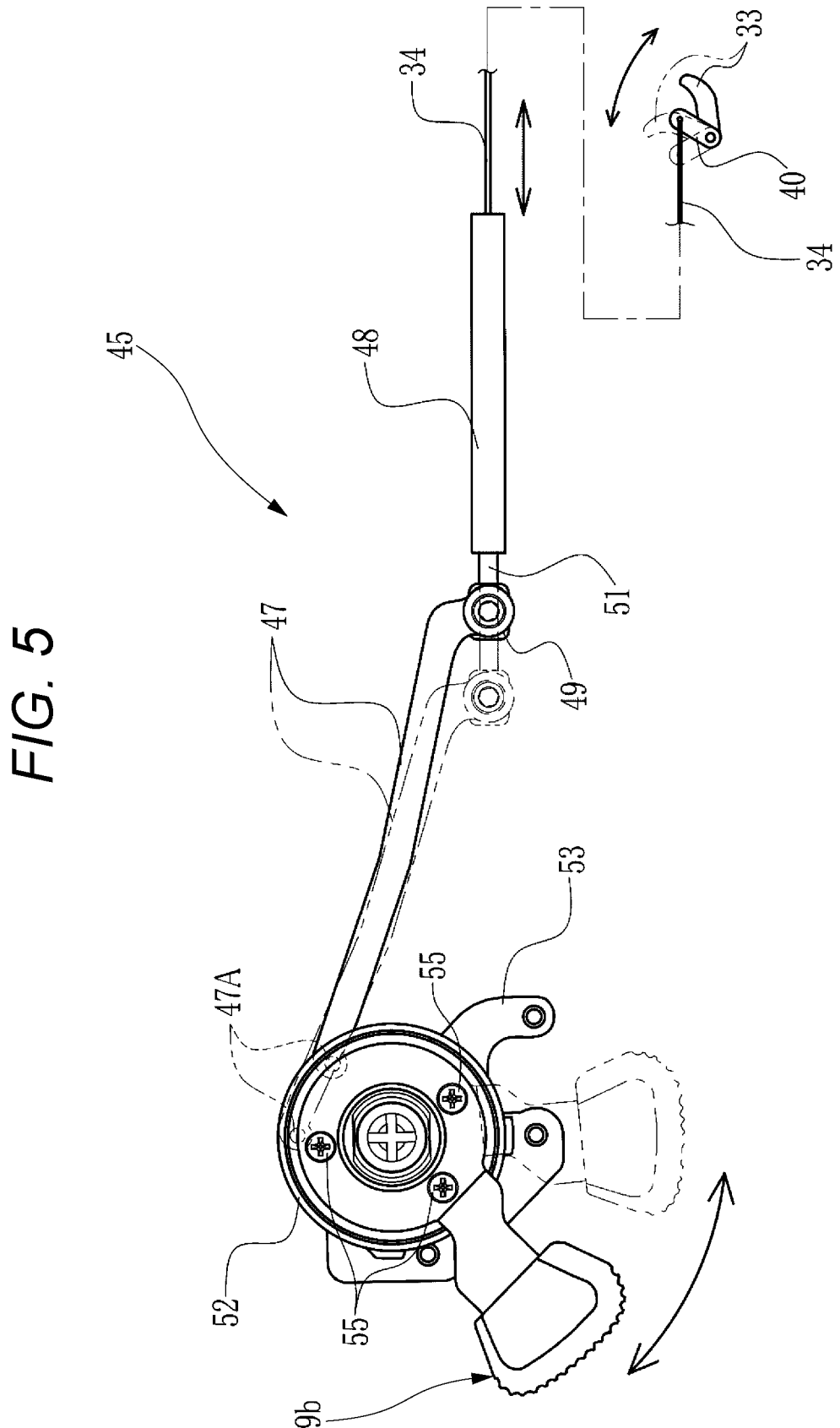
FIG. 5 is a plan view of a treatment tool elevating mechanism.

As illustrated in FIG. 5, the treatment tool elevating mechanism 45 performs operation of pushing and pulling the elevating operation wire 34 according to rotational operation of the elevating operation lever 19*b*. Pushing and pulling the elevating operation wire 34 causes the rotation shaft member 40 and the elevating base 33 described above to rotate. The elevating operation lever 19*b* is operated with a thumb T (refer to FIG. 7).

Figure 6:
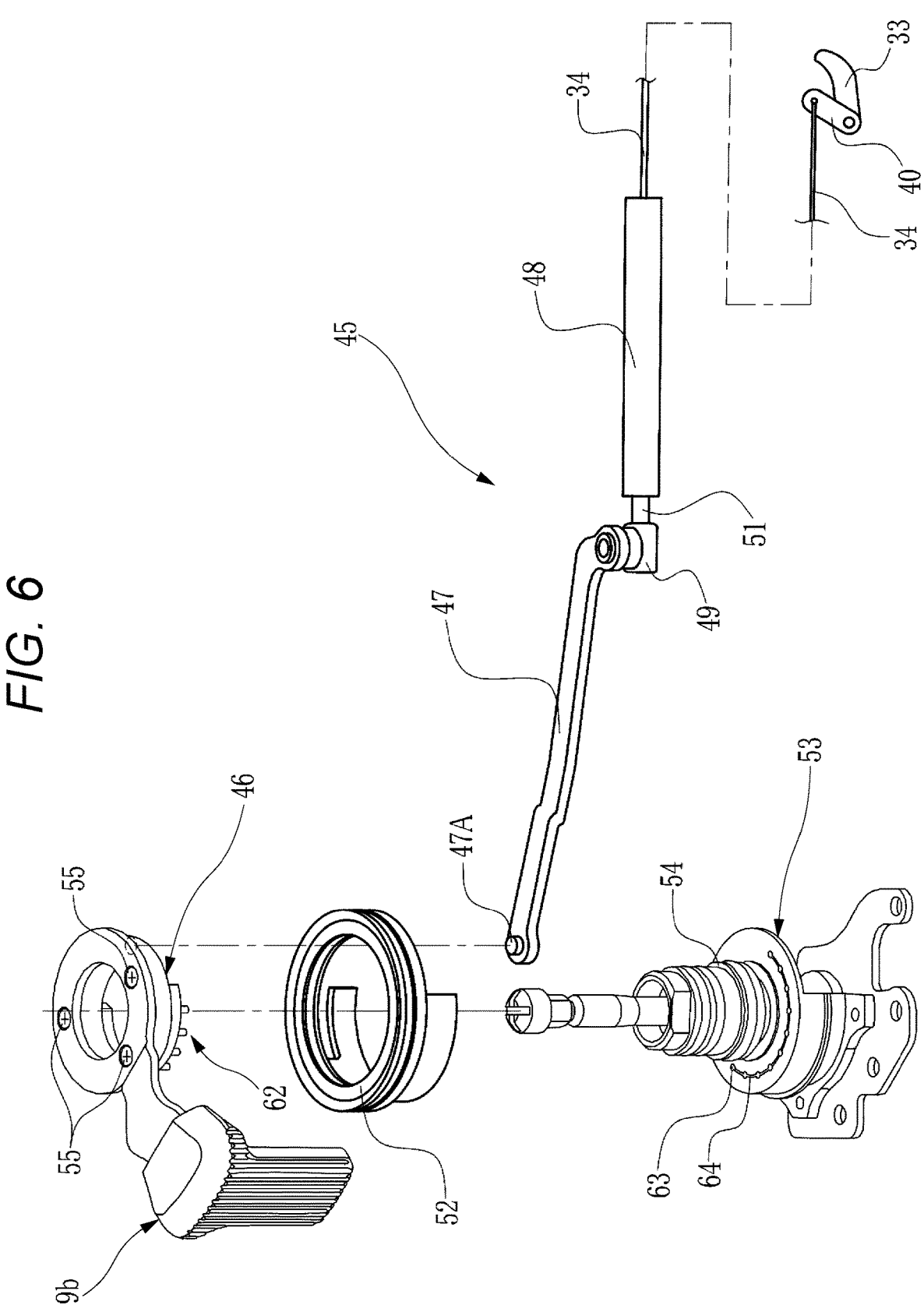
FIG. 6 is an exploded perspective view of the treatment tool elevating mechanism.

As illustrated in FIG. 6, the treatment tool elevating mechanism 45 includes the elevating operation lever 19*b*, a rotation ring 46, a crank member 47, a guide tube 48, a coupling head 49, a slider 51, a fixed ring 52, and a bearing member 53. The rotation ring 46 is formed in a cylindrical shape. The rotation ring 46 is a coupling member that couples the elevating operation lever 19*b* and the bearing member 53.

The bearing member 53 is provided with a rotation shaft 54. The rotation ring 46 is coaxially and rotatably attached to the rotation shaft 54. The bearing member 53 and the fixed ring 52 hold the rotation ring 46. The fixed ring 52 supports an outer peripheral surface of the rotation ring 46 and is fixed to a case 19*f* (refer to FIG. 7) configuring an exterior of the operation part 19. The fixed ring 52 prevents the rotation ring 46 from disengaging from the operation part 19. A coupling member is not limited to a cylindrical shape like the rotation ring 46.

The elevating operation lever 19*b* is coupled to the rotation ring 46, for example, by screwing with a screw 55. One end of the crank member 47 is rotatably coupled to the elevating operation lever 19*b* via a coupling pin 47A, and the other end of the crank member 47 is coupled to the coupling head 49. The slider 51 has one end to which the coupling head 49 is attached and the other end to which the elevating operation wire 34 is coupled. The slider 51 is slidably supported by the guide tube 48. The guide tube 48 is fixed to the case 19*f* (refer to FIG. 7).

Figure 7:
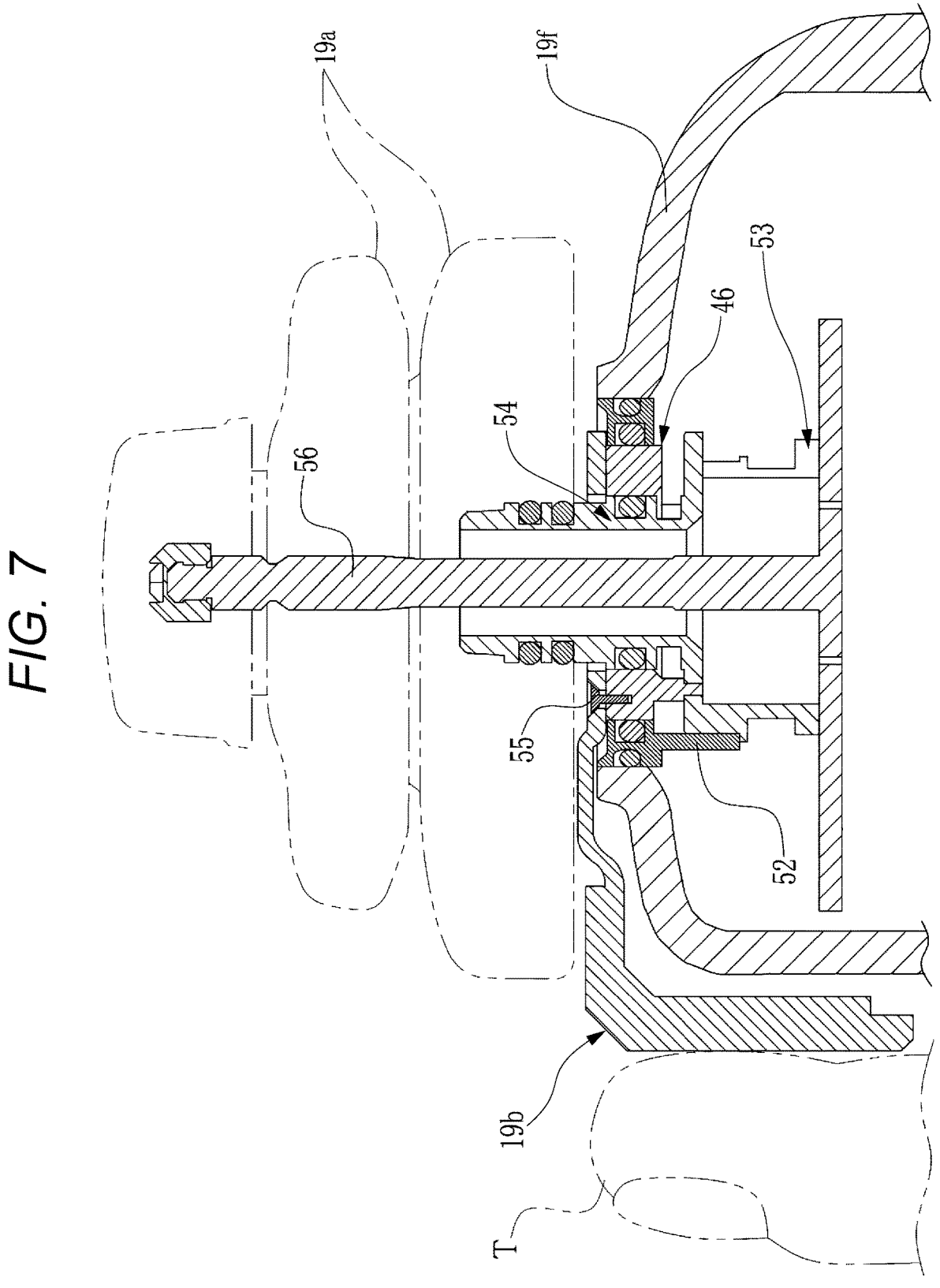
FIG. 7 is a cross-sectional view of main parts around an elevating operation lever and a locking mechanism.

As shown in FIG. 7, the bearing member 53 is fixed to the case 19*f*. The rotation shaft 54 is formed hollow. An attachment shaft 56 of the angle knob 19*a* is inserted into the rotation shaft 54 and fixed thereto. As a result, the angle knob 19*a* is attached to the rotation shaft 54 via the attachment shaft 56. In FIG. 7, illustration of an internal mechanism of the angle knob 19*a*, a mechanism for curving operation of the bendable part 18*b*, and the like is omitted in order to prevent complication.

The crank member 47 and the slider 51 convert the rotation caused by the operation of the elevating operation lever 19*b* into linear motion, i.e., into pushing and pulling operation of the elevating operation wire 34. As the elevating operation lever 19*b* rotates in a counterclockwise direction (first direction) by means of the pushing and pulling operation of the treatment tool elevating mechanism 45, the elevating operation lever 19*b* causes the elevating base 33 to move to the elevated position, and as the elevating operation lever 19*b* rotates in a clockwise direction (second direction), the elevating operation lever 19*b* causes the elevating base 33 to be moved to the fallen position.

Figure 8:
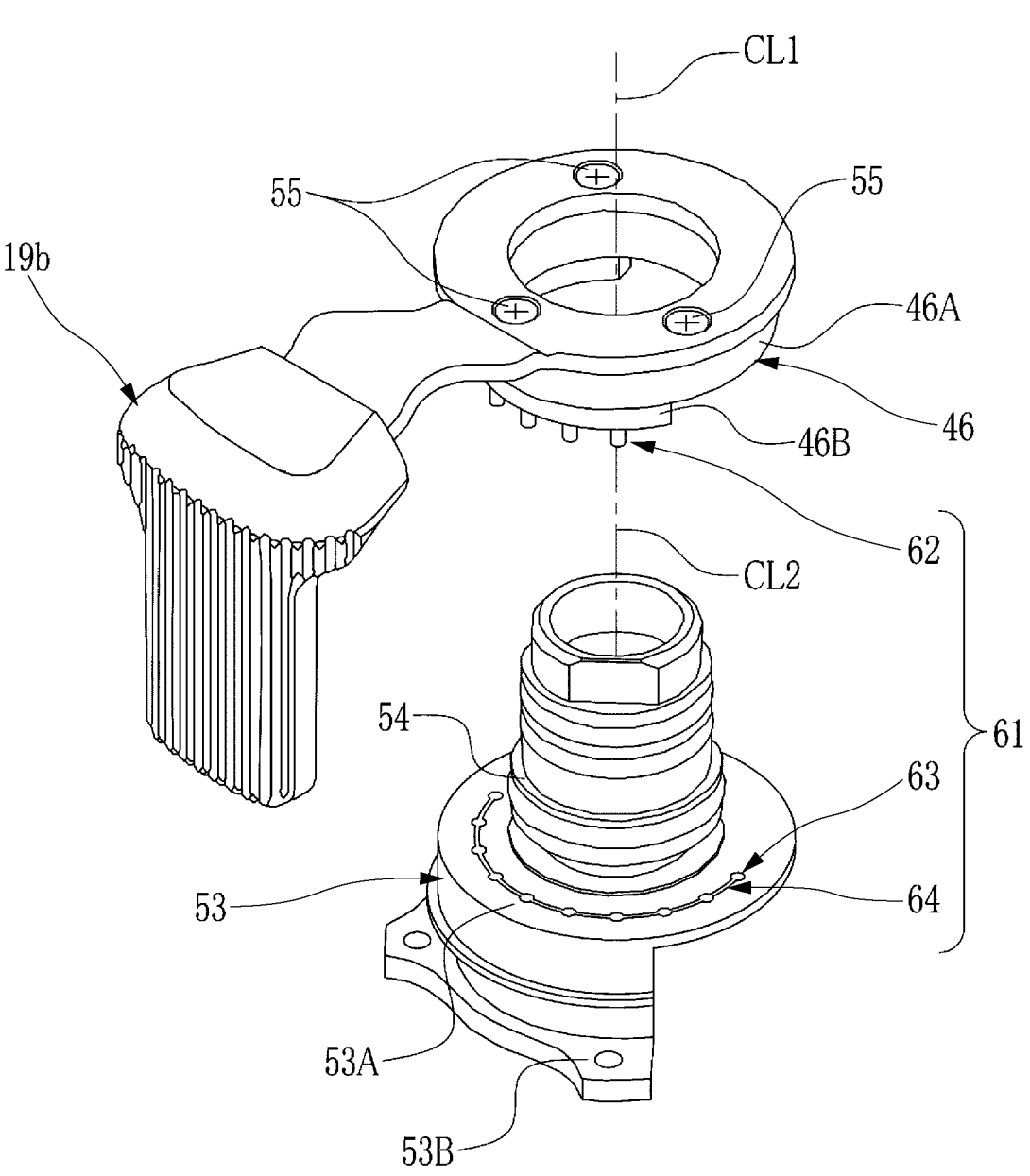
FIG. 8 is a perspective view illustrating a configuration of the locking mechanism.

As illustrated in FIG. 8, a locking mechanism 61 is provided between the bearing member 53 and the rotation ring 46. The locking mechanism 61 has a plurality of protrusions 62, a plurality of holes 63, and a rail 64 positioned between the adjacent holes 63. The protrusions 62 are provided on the rotation ring 46, and the holes 63 and the rail 64 are provided on the bearing member 53.

Figure 9:
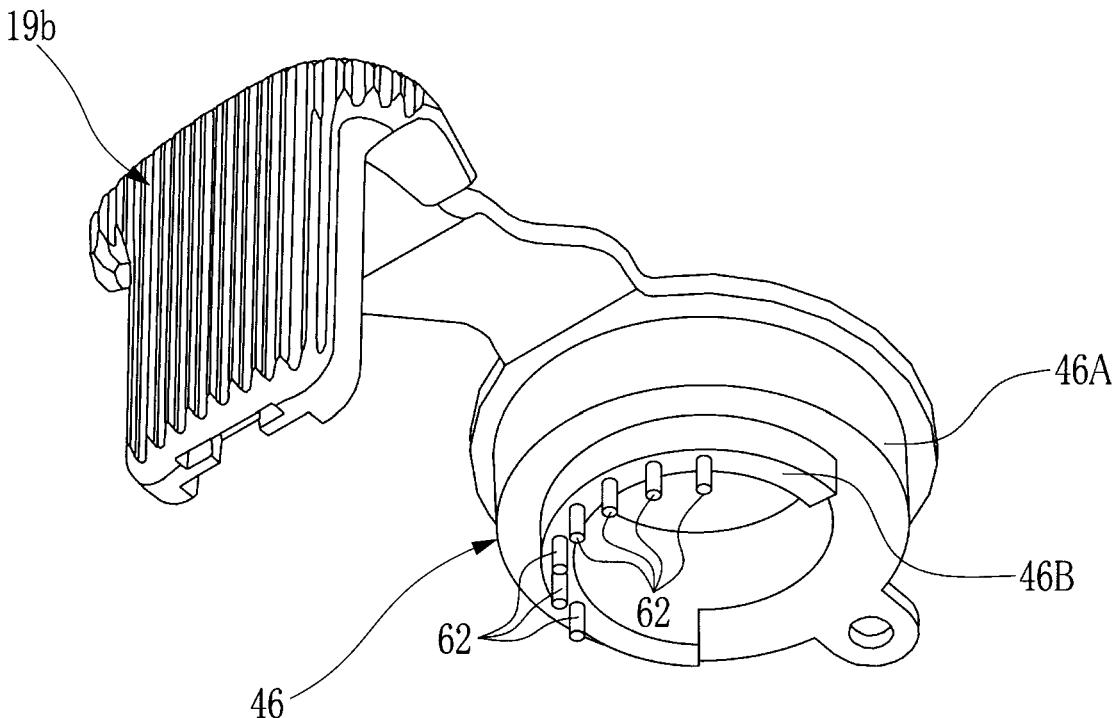
FIG. 9 is a perspective view of a coupling member as viewed from a bottom surface side.

As shown in FIG. 9, the rotation ring 46 has a large diameter part 46A, a small diameter part 46B provided to be continuous with the large diameter part 46A, and the plurality of protrusions 62. The large diameter part 46A is supported by the above-described fixed ring 52. The small diameter part 46B has an outer diameter smaller than that of the large diameter part 46A and is projected on a bottom surface side facing the bearing member 53. A part of the small diameter part 46B is notched so as not to interfere with the operation of the crank member 47. The protrusion 62 is a columnar protrusion that protrudes from the bottom surface side of the small diameter part 46B.

Figure 10:
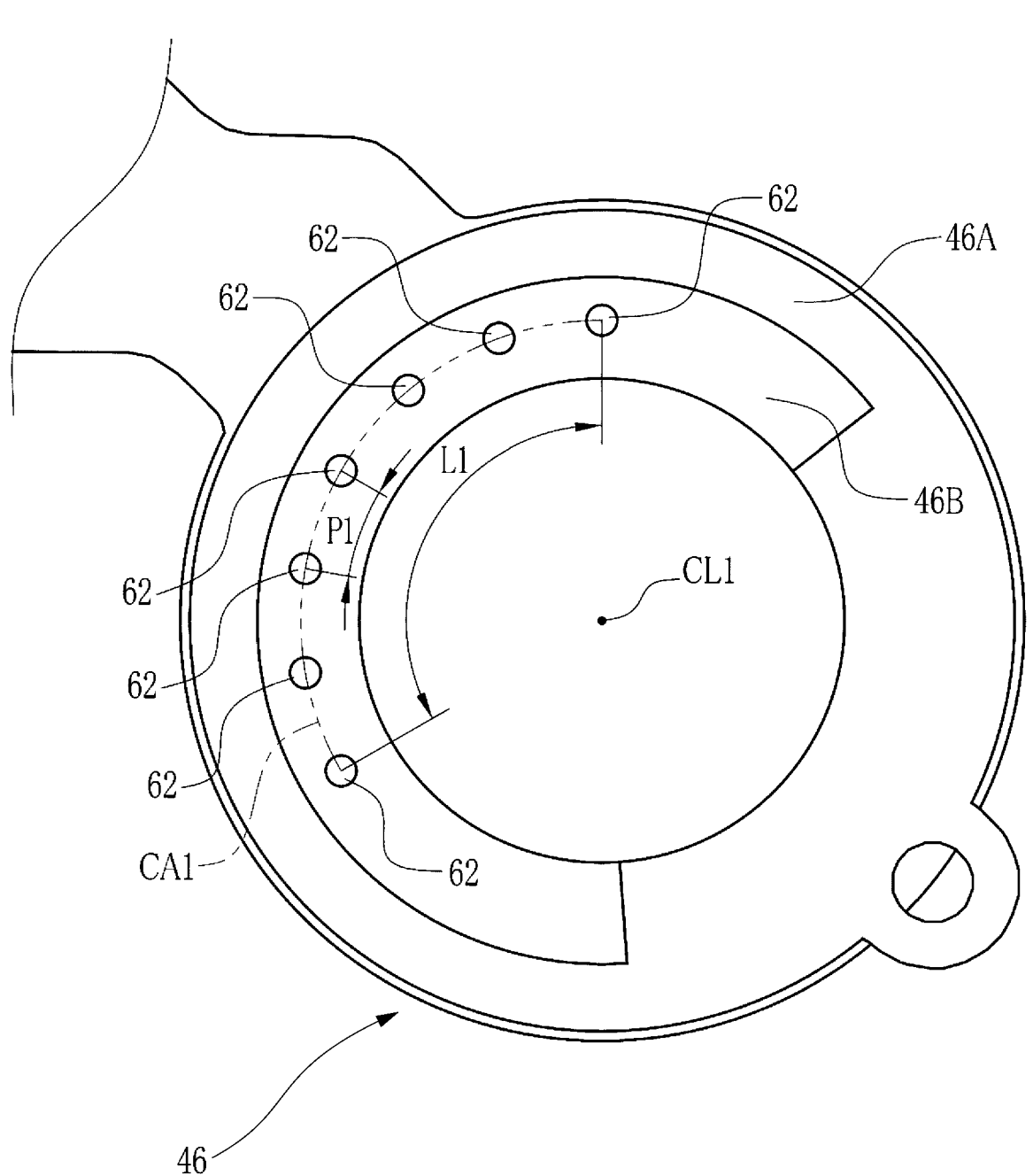
FIG. 10 is a bottom view of the coupling member.

As illustrated in FIG. 10, the protrusions 62 are formed along a first arc CA1 positioned around a center axis CL1 of the rotation ring 46. The protrusion 62 is a columnar protrusion that protrudes from the bottom surface side of the small diameter part 46B. The protrusions 62 are formed along the first arc CA1 positioned around the center axis CL1 of the rotation ring 46. The protrusions 62 are arranged on the first arc CA1 at equal pitches P1.

Figure 11:
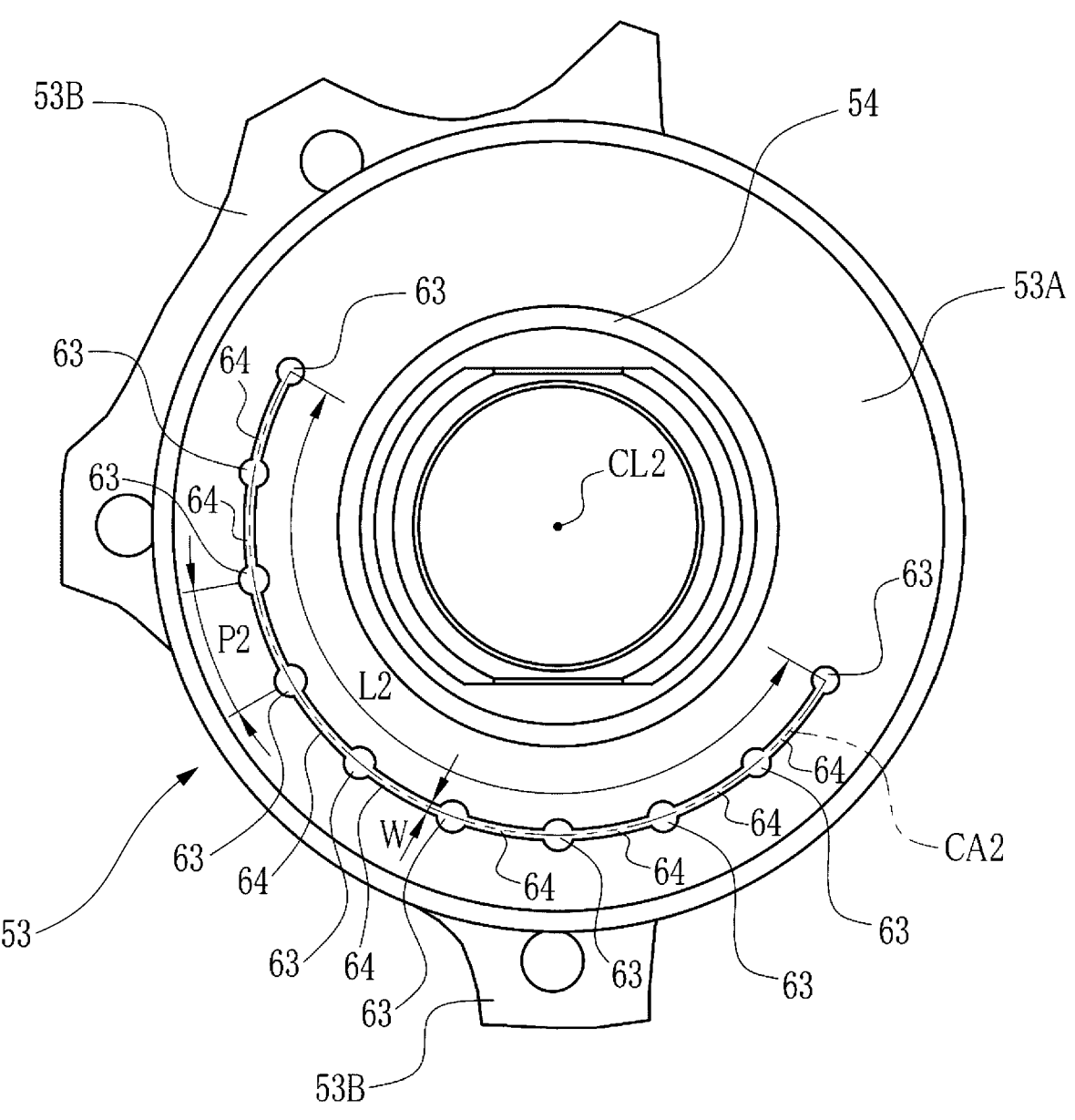
FIG. 11 is a plan view of a bearing member.

As illustrated in FIG. 11, the bearing member 53 has the rotation shaft 54, a support part 53A provided to be continuous with the rotation shaft 54, and a fixed piece 53B. The support part 53A is disposed around the rotation shaft 54 and is formed in a cylindrical shape. The fixed piece 53B protrudes from an outer peripheral surface of the support part 53A, and is fixed to the case 19*f* by, for example, screwing. The hole 63 is a through hole opened in a columnar shape from an upper surface of the support part 53A. The holes 63 are formed along a second arc CA2 positioned around a center axis CL2 of the rotation shaft 54. The second arc CA2 has a radius equal to that of the first arc CA1, and the second arc CA2 has an arc length L2 longer than an arc length L1 of the first arc CA1. The holes 63 are arranged on the second arc CA2 at equal pitches P2.

The pitch P2 of the holes 63 is the same as the pitch P1 of the protrusions 62, and the number of the protrusions 62 is smaller than the number of the holes 63. Although in the present embodiment, the number of the protrusions 62 is seven and the number of the holes 63 is ten, the numbers of the protrusions 62 and the holes 63 are not limited thereto, and the number of the protrusions 62 need only be smaller than the number of the holes 63 by at least one.

The hole 63 is formed to have an inner diameter in accordance with an outer diameter of the protrusion 62, whereby the hole 63 and the protrusion 62 are fitted to each other. The rail 64 is disposed between the holes 63 along the second arc CA2. When the rail 64 is not pressed by the protrusion 62, a width W of the rail 64 is smaller than the outer diameter of the protrusion 62. Accordingly, when the rail 64 is not pressed by the protrusion 62, the protrusion 62 is not allowed to pass through the rail 64. In other words, the movement of the protrusion 62 is restricted. Meanwhile, when the elevating operation lever 19*b* is rotationally operated, the rail 64 is elastically deformed by pressing received from the protrusion 62. In other words, the rail 64 becomes wider than the above-described width W. This allows the protrusion 62 to move.

Figure 12A:
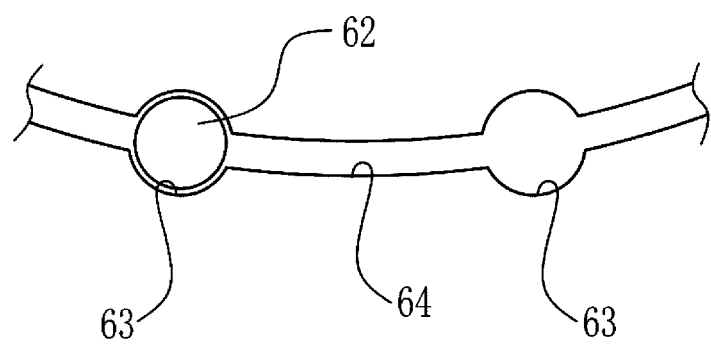
FIGS. 12A to 12C are views illustrating operation of the locking mechanism.

As shown in FIG. 12A, when the protrusion 62 is fitted to the hole 63, the movement of the protrusion is restricted by the rail 64 as described above. In other words, the elevating operation lever 19*b* is locked at the first position. A state in which the protrusion 62 is fitted to the hole 63 here represents a state in which each protrusion 62 is fitted to any one of the holes 63. Note that FIGS. 12A to 12C are views for explanation focusing only on one protrusion 62, and are different from the actual configurations.

Figure 12B:
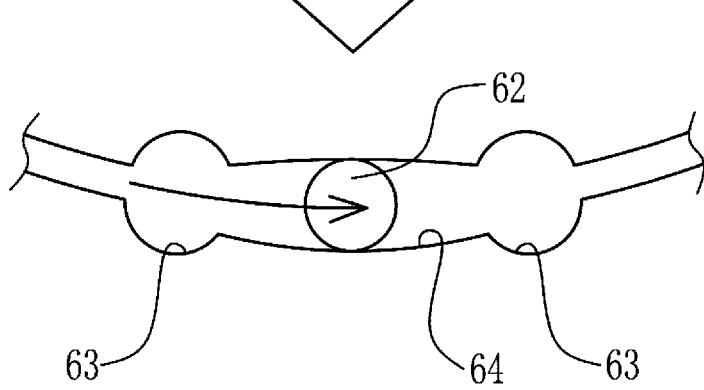
Figure 12C:
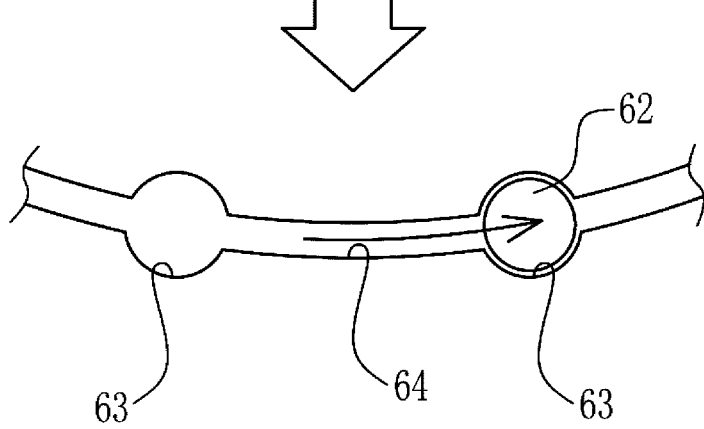

As shown in FIG. 12B, when the elevating operation lever 19*b* is rotated counterclockwise or clockwise, the rail 64 is elastically deformed by the pressing force received from the protrusion 62. As described above, the protrusion 62 is allowed to move. As illustrated in FIG. 12C, the protrusion 62 passes through the elastically deformed rail 64 and moves to the hole 63 at a position different from the first position, and the elevating operation lever 19*b* is locked at the second position.

A fitting strength between the protrusion 62 and the hole 63 in a case where the elevating base 33 is at the elevated position needs to be high enough to prevent the protrusion 62 from detaching from the hole 63, i.e., to prevent the elevating operation lever 19*b* from moving even when a reaction force is received from the treatment tool 13. In addition, it is preferable that the fitting strength between the protrusion 62 and the hole 63 in a case where the elevating base 33 is at the fallen position is also a high fitting strength equivalent to that in the case where the elevating base is at the elevated position. That is, in a case where the elevating base 33 is rotated from the elevated position to the fallen position, the elevating base tends to rotate in a direction of returning to the elevated position due to a reaction force received by the distal end part main body 31. If the reaction force is so strong that the elevating base 33 rotates to the elevated position, the treatment tool 13 might enter an observation range of the endoscope 12 in a situation not intended by a user. Therefore, it is preferable that even in the case where the elevating base 33 is at the fallen position, the fitting strength between the protrusion 62 and the hole 63 has a high fitting strength equivalent to that in the case where the elevating base is at the elevated position.

Figure 13:
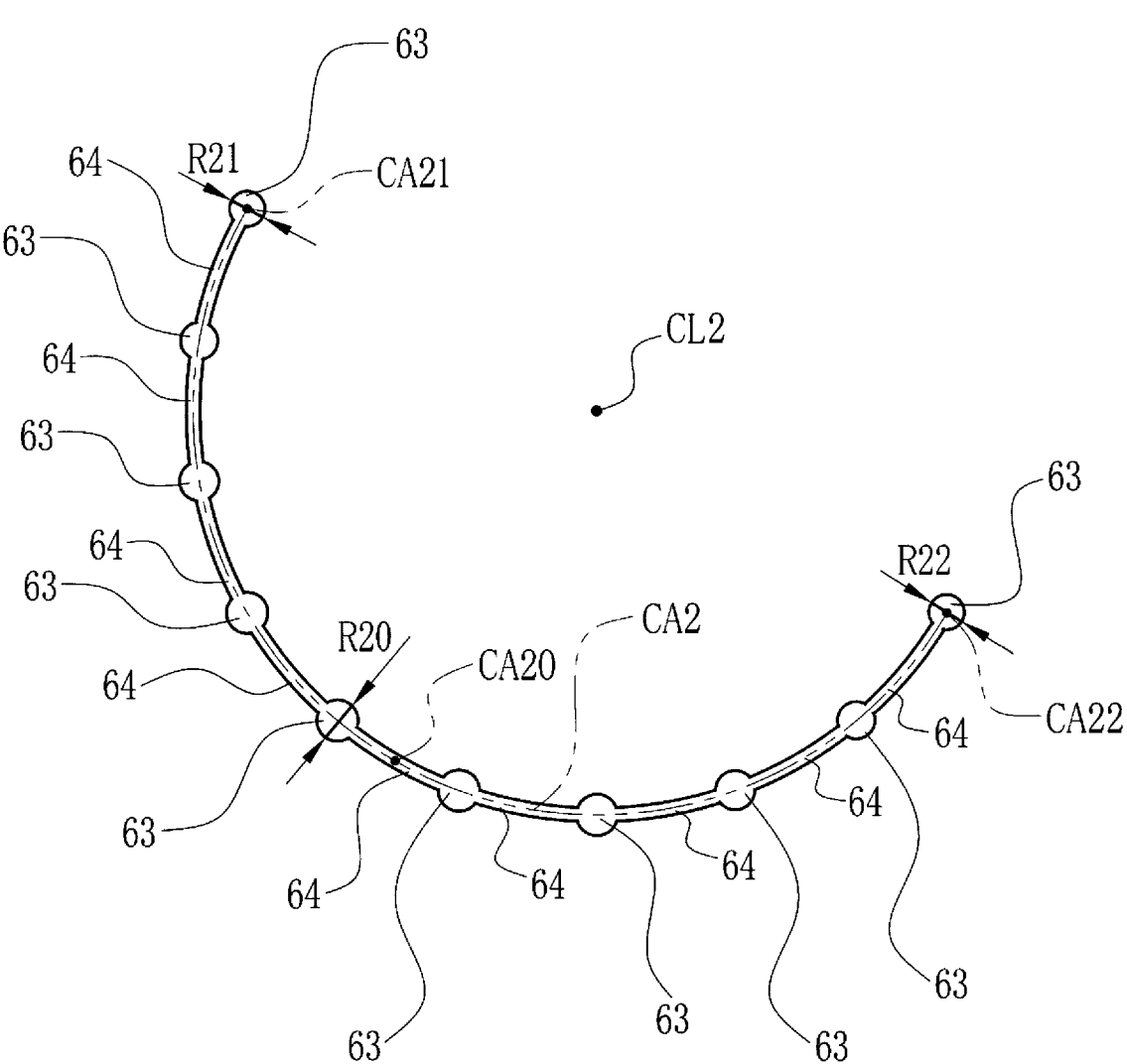
FIG. 13 is a plan view of a hole constituting the locking mechanism.

As illustrated in FIG. 13, the inner diameter of the hole 63 is formed to gradually decrease from an intermediate portion of the second arc CA2 toward both ends CA21 and CA22. In the present embodiment, an inner diameter R20 of the hole 63 closest to a center CA20 in a circumferential direction of the second arc CA2 is the largest, and inner diameters R21 and R22 of the holes 63 positioned at both the ends CA21 and CA22 are the smallest. Accordingly, when the protrusions 62 are fitted to the holes 63 positioned at both ends CA21 and CA22 of the second arc CA2, the protrusions 62 are least likely to be detached from the holes 63.

The holes 63 located at both ends CA21 and CA22 of the second arc CA2 and the protrusions 62 are fitted to each other at both ends of a range in which the elevating operation lever 19*b* is rotatable. In other words, in a case where the elevating base 33 is at the fallen position or the elevated position, the holes 63 located at both ends CA21 and CA22 of the second arc CA2 and the protrusions 62 are fitted to each other. Therefore, in the case where the elevating base 33 is at the fallen position or the elevated position, the protrusions 62 are least likely to be detached from the holes 63.

Description will be made of operation which is performed by a doctor as a user when inserting the treatment tool 13 into the treatment tool channel 18*d* of the endoscope 12 and conducting treatment on a patient as a subject. The doctor inserts the insertion part 18 of the endoscope 12 into a body of the patient. Furthermore, the treatment tool 13 is inserted into the treatment tool channel 18*d* through the treatment tool lead-in port 19*c*. The treatment tool 13 inserted into the treatment tool channel 18*d* is led out of the treatment tool lead-out port 18*e* into the subject. In the case where the elevating base 33 is at the fallen position, the treatment tool

13 is not elevated at all. In this case, the treatment tool 13 is not present in the observation range imaged by the image sensor 43. For example, the doctor rotationally operates the elevating operation lever 19*b* to move the elevating base 33 from the fallen position to the elevated position in order to make the treatment tool 13 enter the observation range.

As described above, since the endoscope 12 includes the locking mechanism 61, the elevating operation lever 19*b* is locked when the protrusion 62 is fitted to the hole 63. Then, when the doctor rotationally operates the elevating operation lever 19*b* in the counterclockwise direction in order to elevate the treatment tool 13, the rail 64 is elastically deformed by the pressing force received from the protrusion 62 to allow the protrusion 62 to move. Then, the protrusion 62 passes through the rail 64 to move to the different hole 63, so that the elevating operation lever 19*b* is locked. In this manner, the doctor rotationally operates the elevating operation lever 19*b* to rotate the elevating base 33, and the locking mechanism 61 operates. As a result, a lead-out direction of the treatment tool 13 can be changed to a desired direction. For example, the doctor determines that the lead-out direction of the treatment tool 13 is changed to a desired direction when the distal end part 22 of the treatment tool 13 enters the observation range imaged by the image sensor 43.

As described above, when the doctor changes the lead-out direction of the treatment tool 13 in a desired direction, the elevating base 33 may be at a position in the middle of the fallen position and the elevated position. In this case, the doctor stops the rotational operation of the elevating operation lever 19*b*. This also makes the movement of the protrusion 62 stop, so that the elevating operation lever 19*b* is brought into a locked state. Since the elevating operation lever 19*b* is locked, the doctor can perform treatment in a state where the lead-out direction of the treatment tool 13 is maintained at the desired direction. Even if a treatment is performed in this state and a reaction force is received from the treatment tool 13, the elevating operation lever 19*b* will not move. As a result, the elevating base 33 does not move either, and the lead-out direction of the treatment tool 13 will not deviate. By leading the distal end part 22 of the treatment tool 13 led out from the opening window 32C in a state in which the lead-out direction is maintained at the desired direction, the doctor can perform various treatments such as resection and collection of an observation site.

Additionally, when the elevating base 33 is at the elevated position, the treatment tool 13 in many cases moves forward and backward in the treatment tool channel 18*d* to perform the operation of the distal end part 22. In this case, as described above, the elevating operation lever 19*b* receives the largest reaction force from the treatment tool 13 through the elevating base 33, the elevating operation wire 34, the treatment tool elevating mechanism 45, and the like. Furthermore, even in the case where the elevating base 33 is at the fallen position, since the elevating base 33 tends to rotate due to the received reaction, the elevating operation lever receives a large reaction force through the elevating base 33, the elevating operation wire 34, the treatment tool elevating mechanism 45, and the like. Meanwhile, in the present invention, since the hole 63 is formed to have the inner diameter that gradually decreases from the intermediate portion of the second arc CA2 toward both ends, the protrusion 62 is least likely to be detached from the hole 63 when the elevating base 33 is at the fallen position or the elevated position. Therefore, for example, even when the treatment tool 13 having a large reaction force such as a stent or a puncture needle is used, the position of the elevating operation lever 19*b* will not deviate when the elevating base 33 is at the elevated position or the fallen position.

Although the above embodiment illustrates, as an example, a case where the elevating base 33 is rotated from the fallen position toward the elevated position to direct the treatment tool 13 in a desired direction, the present invention is not limited thereto, and even in a case of rotating the elevating base 33 from the elevated position toward the fallen position, the locking mechanism 61 operates to lock the elevating operation lever 19*b* as in the above embodiment. Then, various treatments can be performed while the lead-out direction of the treatment tool 13 is maintained at a desired direction. Although the above embodiment illustrates, as an example, a case where the first direction is set as the counterclockwise direction and the second direction is set as the clockwise direction, the first direction may be set as the clockwise direction and the second direction may be set as the counterclockwise direction.

Furthermore, although in the above-described embodiment, the protrusion 62 is provided on the rotation ring 46 as the coupling member, and the plurality of holes 63 and the rail 64 are provided on the bearing member 53, the present invention is not limited thereto, and the plurality of holes 63 and the rail 64 may be provided on the rotation ring 46, and the protrusion 62 may be provided on the bearing member 53.

EXPLANATION OF REFERENCES

10: Endoscope system
12: Endoscope
13: Treatment tool
14: Light source device
15: Processor device
16: Display
17: User interface (UI)
18: Insertion part
18*a*: Flexible part
18*b*: Bendable part
18*c*: Distal end part
18*d*: Treatment tool channel
18*e*: Treatment tool lead-out port
19: Operation part
19*a*: Angle knob
19*b*: Elevating operation lever
19*c*: Treatment tool lead-in port
19*d*: Air/water supply button
19*e*: Suction button
19*f*: Case
21: Flexible sheath
22: Distal end part
23: Operation part
31: Distal end part main body
32: Cap
32A: Peripheral surface portion
32B: End surface portion
32C: Opening window
33: Elevating base
34: Elevating operation wire
35: Signal cable
36: Light guide
37: Disk part
38: Partition wall part
39: Partition wall part
41: Elevating base accommodation part
42: Air/water supply nozzle
43: Image sensor
44: Illumination optical system
45: Treatment tool elevating mechanism
46: Rotation ring
46A: Large diameter part
46B: Small diameter part
47: Crank member
47A: Coupling pin
48: Guide tube
49: Coupling head
51: Slider
52: Fixed ring
53: Bearing member
53A: Support part
53B: Fixed piece
54: Rotation shaft
55: Screw
56: Attachment shaft
61: Locking mechanism
62: Protrusion
63: Hole
64: Rail
CL1: Center axis
CL2: Center axis
CA1: First arc
CA2: Second arc
CA20: Center
CA21: End portion
CA22: End portion
L1: Arc length
L2: Arc length

What is claimed is:

1. An endoscope comprising:

an insertion part to be inserted into a subject;

an operation part provided at a proximal end of the insertion part;

a distal end part main body that is positioned at a distal end of the insertion part and that communicates with a treatment tool lead-out port;

an elevating base that is provided on the distal end part main body and that causes a treatment tool led out from the treatment tool lead-out port to elevate, the elevating base being provided to be movable between an elevated position and a fallen position;

an elevating operation lever that rotates in a first direction to move the elevating base to the elevated position and that rotates in a second direction to move the elevating base to the fallen position;

a bearing member provided in the operation part;

a coupling member that couples the elevating operation lever and the bearing member; and a locking mechanism that is provided between the bearing member and the coupling member and that includes:

a plurality of protrusions provided on one of the bearing member and the coupling member;

a plurality of holes provided on the other of the bearing member and the coupling member; and a rail positioned between the plurality of holes adjacent to each other, wherein in a case where at least one protrusion of the plurality of protrusions is fitted to at least one hole of the plurality of holes, the elevating operation lever is locked at a first position, and in a case where the elevating operation lever is rotated in the first direction or the second direction, the at least one protrusion of the plurality of protrusions passes through the rail, wherein the rail elastically deforms as the at least one protrusion of the plurality of protrusions moves to the at least one hole of the plurality of holes at a position different from the first position to lock the elevating operation lever at a second position.

2. The endoscope according to claim 1, wherein the plurality of holes and the plurality of protrusions are formed at a same pitch, and a number of the plurality of protrusions is smaller than a number of the plurality of holes.

3. The endoscope according to claim 2, wherein one of the bearing member and the coupling member has the plurality of protrusions formed along a first arc positioned around a center axis of the coupling member, and the other of the bearing member and the coupling member has the holes formed along a second arc that is positioned around a center axis of a rotation shaft included in the bearing member, that has a radius equal to a radius of the first arc, and that has an arc length longer than an arc length of the first arc.

4. The endoscope according to claim 3, wherein inner diameters of the plurality of holes are formed to gradually decrease from an intermediate portion of the second arc toward both ends of the second arc.

5. The endoscope according to claim 1, wherein the insertion part includes a bendable part, and an angle knob that bends the bendable part is attached to the bearing member.

6. The endoscope according to claim 1, wherein at least one of the insertion part, the operation part, the distal end part main body, the elevating base, the elevating operation lever, the bearing member, the coupling member, and the locking mechanism is disposable.

\* \* \* \* \*